United States Patent [19]  [11]  4,363,080
Sylvester  [45]  Dec. 7, 1982

[54] WATER-COOLED LIGHT SOURCE

[75] Inventor: Donald D. Sylvester, Tigard, Oreg.

[73] Assignee: Dentek Systems, Inc., Tigard, Oreg.

[21] Appl. No.: 182,975

[22] Filed: Sep. 2, 1980

[51] Int. Cl.³ .............................................. F21V 7/04
[52] U.S. Cl. ...................................... 362/32; 362/96;
  362/101; 362/218; 362/294; 362/373; 362/804
[58] Field of Search ................... 362/32, 96, 101, 218,
  362/294, 373, 804

[56] References Cited
U.S. PATENT DOCUMENTS 2,255,657  9/1941  Freedman ............................. 362/96
2,274,893  3/1942  Freedman ............................. 362/96
4,009,382  2/1977  Nath .................................... 362/32
4,171,572  10/1979  Nash .................................... 362/32

Primary Examiner—Stephen J. Lechert, Jr.
Attorney, Agent, or Firm—Kolisch, Hartwell & Dickinson

[57] ABSTRACT

Apparatus for supplying a source of light, in a dental control unit, to an optical fiber for transmission of light from the source, along the fiber, into a patient's mouth. A heat sink is provided with a cavity for receiving a high intensity light. A duct leads from the light to the exterior of the heat sink to permit access of the fiber to the light. The block contains a fluid-conducting bore therethrough for conducting heat from the block to the fluid.

5 Claims, 5 Drawing Figures

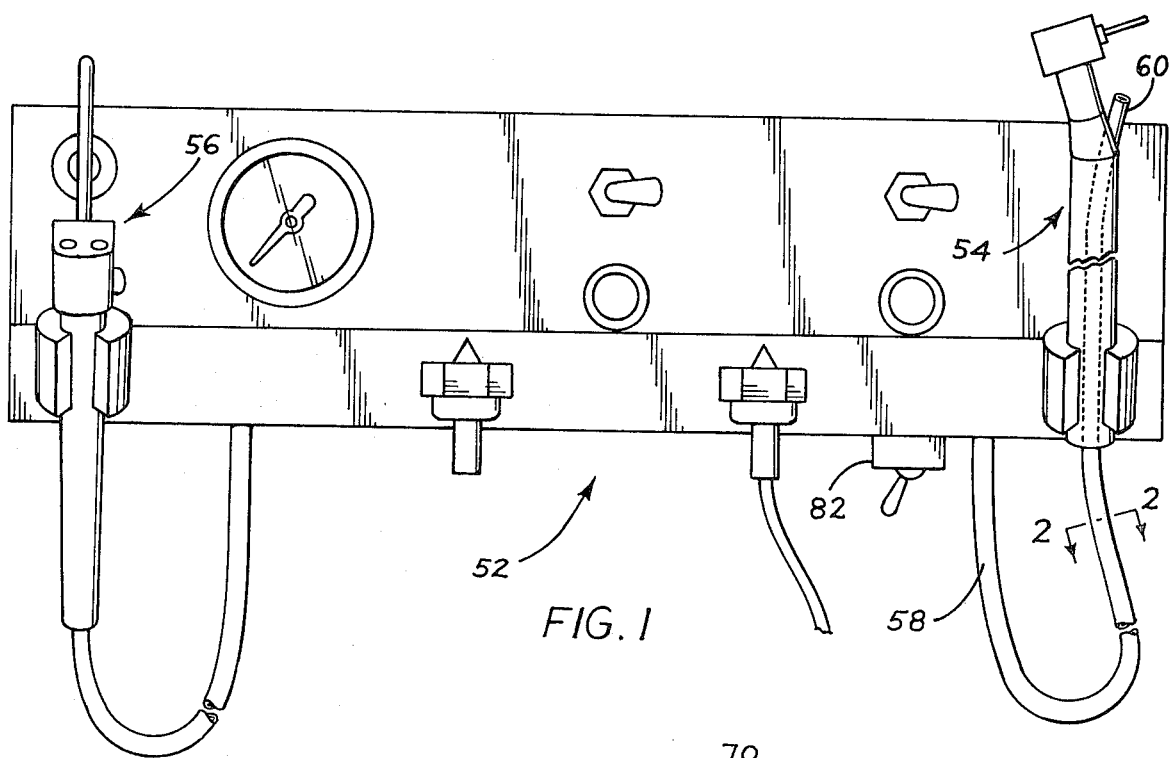
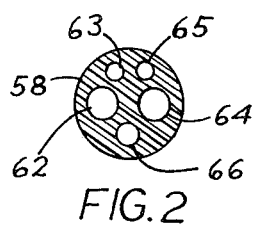
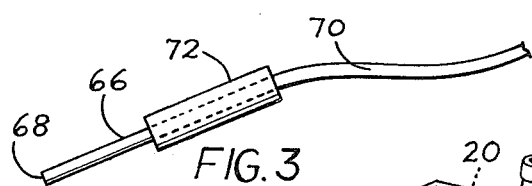
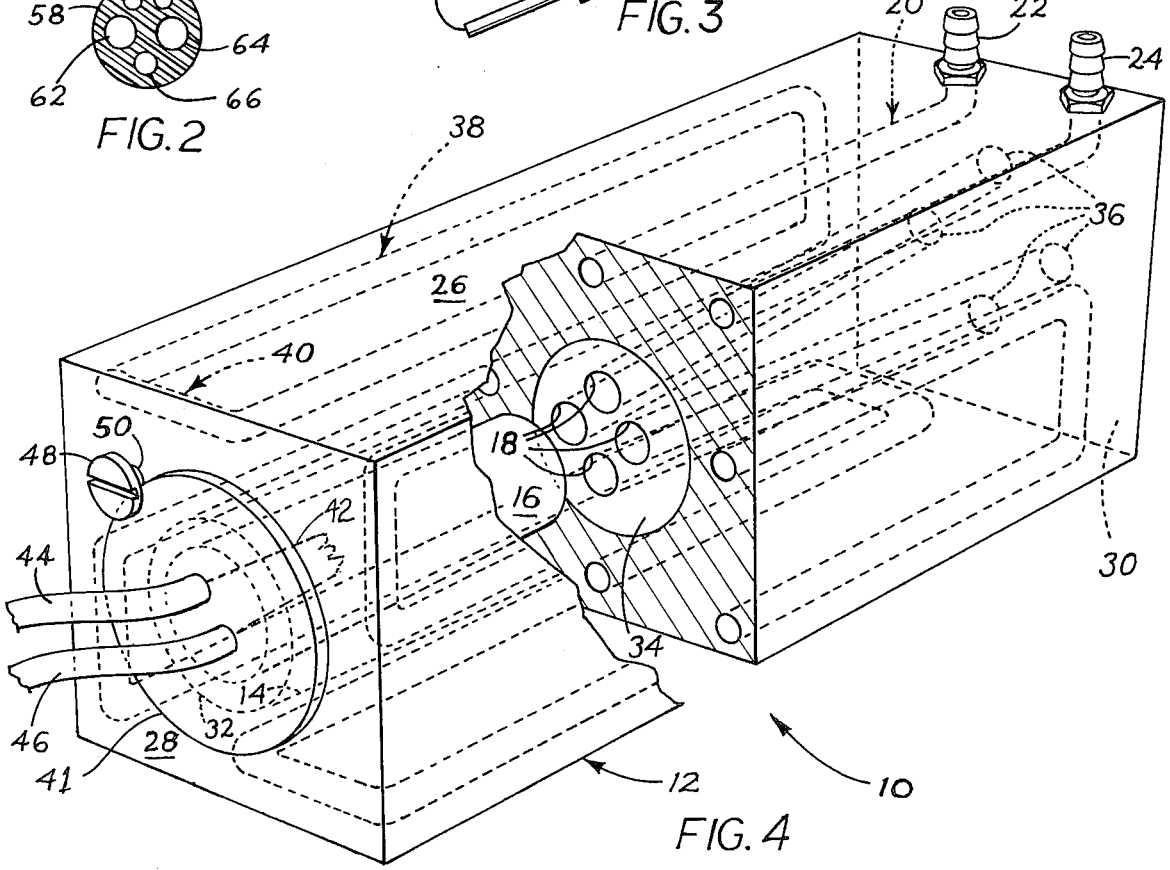

WATER-COOLED LIGHT SOURCE

BACKGROUND AND SUMMARY OF THE INVENTION

This invention relates to light sources for supplying light for transmission along a bundle of fiber optics, and, more particularly, to such a source which is water cooled.

It is old in the art to shine a light upon one end of a bundle of optic fibers for transmission of light along the bundle. One such application is in dentistry. A light source transmits light into one end of a bundle of optic fibers, the other end of which is positioned on a dental handpiece for providing illumination of a patient's mouth so that the dentist can better see his work. In order to transmit sufficient light, a relatively high intensity light is required. Such lamps, especially when placed in an enclosure, require cooling. In the past, devices which provide light sources for use with fiber optics in dental handpieces have included a fan to cool the light bulb. Such a device is typically contained within its own cabinet, like those disclosed in U.S. Patents Cawood, 4,025,776, Scrivo et al, 3,758,951 and Keller, 3,638,013.

It is a general object of the present invention to provide a light source for use with a fiber optic system which is small, noiseless, and, in the case of a dental application, may be easily inserted into an existing dental control unit.

According to a preferred embodiment of the invention, a metal block is provided which has a bore at one end thereof suitable for receiving a conventional quartz-halogen light. Ducts are provided at the end of the bore leading from the light source to one face of the block, the ducts being suitable to each receive a fiber optic bundle. Passing through the block is a conduit having an inlet and an outlet, the conduit being formed in a zig-zag manner about the bore containing the light. When the light is on, water flows through the conduit thus cooling the block and the light.

These and other objectives and advantages attained by the invention will become more fully apparent when read in view of the following drawings and accompanying described.

DESCRIPTION OF THE DRAWINGS

FIG. 1 is a perspective view of a dental control unit with the invention contained therein.

FIG. 2 is an enlarged cross-sectional view taken along line 2—2 in FIG. 1.

FIG. 3 is a partial perspective view of a fiber optic bundle and its associated connector.

FIG. 4 is an enlarged perspective view of the instant embodiment of the invention with a portion thereof broken away.

DETAILED DESCRIPTION OF THE INVENTION

Figure 5:
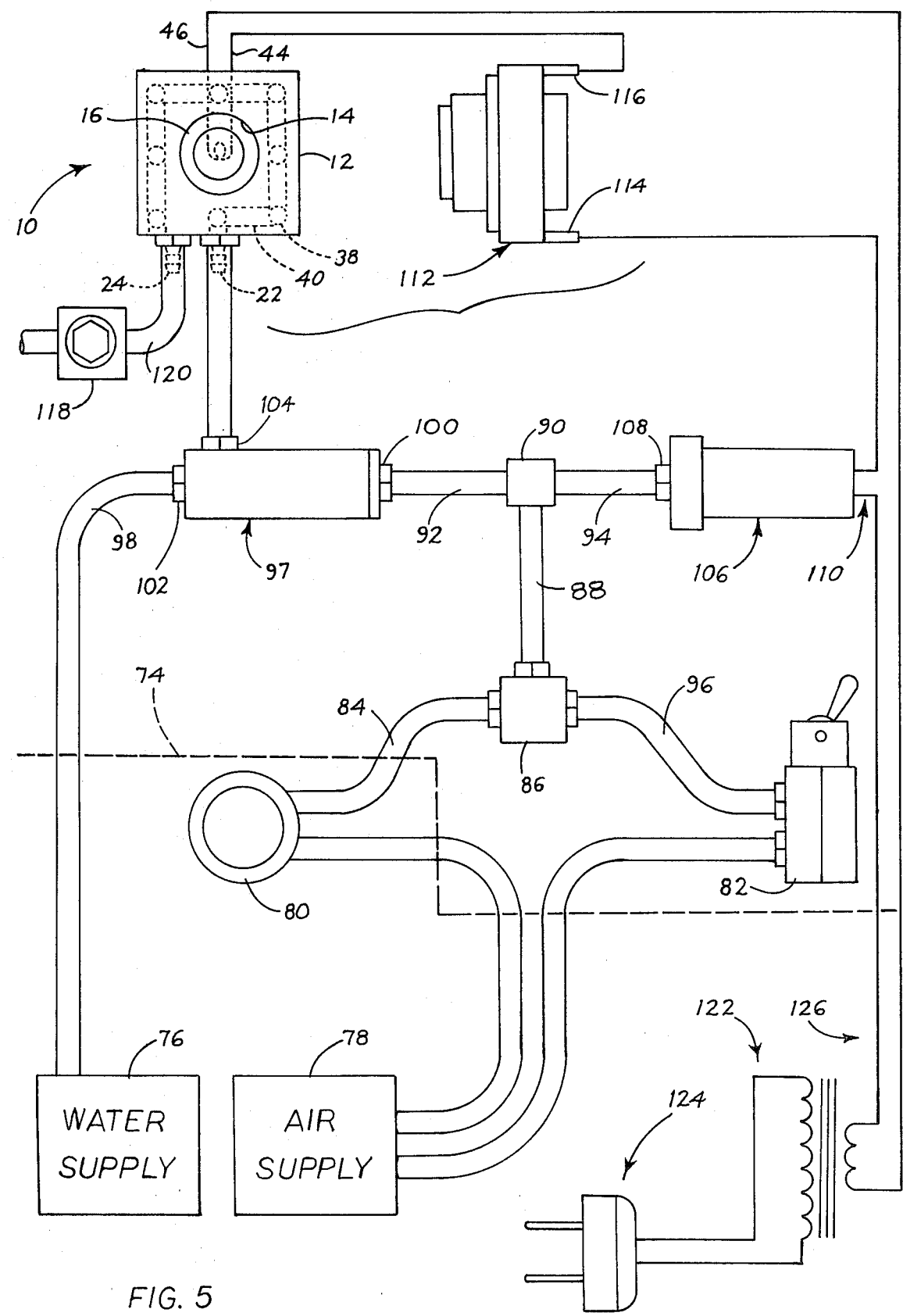
FIG. 5 is a schematic diagram which includes the instant embodiment of the invention.

Turning now to the drawings, a preferred embodiment of the invention is indicated generally at 10. Speaking generally, a heat sink 12, such being a generally block-shaped piece of brass, includes a cavity 14 which receives a high intensity light 16. Ducts 18 define a passage from the cavity to the exterior of the block. A bore 20, such having an inlet 22 and an outlet 24 zig-zags throughout sink 12 as shown in FIG. 4.

When it is desired to supply light to one end of a conventional fiber-optic bundle for transmission of light along the bundle, the bundle end is placed into one of ducts 18. A fluid supply, typically water, is connected to inlet 22. When light 16 is energized, thus transmitting light along the fiber-optic bundle, water is pumped into inlet 22 through bore 20, and out of outlet 24. Such action provides the necessary light to the fiber-optics bundle while cooling the light.

Examining more particularly now the structure of heat sink 12, included within the sink are eight faces, one of which is a top face 26, two other such faces being end faces 28, 30. Included within end face 28 is an entrance 32 to cavity 14. As can be seen in the instant embodiment of the invention, cavity 14 is a circular bore having a bottom face 34. In the view of FIG. 4, heat sink 12 is cut away between the bottom face 34 and approximately midway along cavity 14.

Ducts 18 provide communication between cavity 14 and the exterior of the block, the ends 36 of ducts 18 appearing in end face 30 of the heat sink. The ducts are oriented so that their axes are aimed at a filament 42 within the lamp.

A bore 20, also referred to herein as passage defining means or means defining a plurality of conduits, includes multiple conduits, one of which is indicated at 38, which define passageways oriented normal to faces 28, 30. Also included within bore 20 are conduit connectors, one such being indicated at 40. The conduit connectors are bores which are oriented parallel to faces 28, 30 and connect adjacent conduits at one end thereof. Thus, bore 20 runs continuously throughout the sink between inlet 22 and outlet 24.

Light 16 is a conventional quartz-halogen light, and, in the instant embodiment of the invention requires 12 volts and dissipates 55 watts of power. Included within light 16 is a base 41, filament 42 and wires 44, 46. Light 16 is received within the cavity so that the base of the light is flush against face 28. A screw 48, received within a threaded bore 50 in the heat sink, secures the base against face 28.

Indicated generally at 52 in FIG. 1 is the exterior of a conventional dental control unit. Such is typically mounted adjacent a dentist's chair so that the dentist may have easy access to, for example, a drill 54 or a syringe 56, such being used to rinse a patient's mouth. In the typical dental control unit drill 54 is air powered and also includes water and air outlets adjacent the drill bit to provide a water flow for washing away drilling debris and to cool the bit. The water and air are supplied in tubes contained within drill cable 58. Cable 58 also includes a conventional fiber-optic bundle, such having one end 60 thereof adjacent the drill bit for shining light into the patient's mouth. Typically the fiber-optic bundle is not included within a cable, like cable 58, but descends from an overhead light or from a separate light source. In the instant embodiment of the invention, the fiber-optic bundle is included within the cable which has one end thereof in control unit 52. FIG. 2 is a cross section of the cable showing a drill drive-air line 62 and a drill exhaust-air line 64. Also included within the cable is an air coolant line 63, a water coolant line 65, and a fiber-optic bundle 66.

FIG. 3 is a view of the other end 68 of fiber-optic bundle 66 separated both from the control unit and from the instant embodiment of the invention. Bundle 66 is covered with vinyl 70 between a metal grip 72 and end 60 of the fiber-optic bundle. When the structure illustrated in FIG. 3 is in place within the dental control unit, the vinyl-covered portion of the fiber-optic bundle extends from grip 72, and joins lines 62, 63, 64, 65 to form cable 58 which exits the unit and is attached to drill 54.

Attention is directed to FIG. 5 for a description of the electric, water, and air interconnections included within the instant embodiment of the invention. Firstly, FIG. 5 is split into two portions by dashed line 74. Components appearing above 74 are, in the instant embodiment of the invention, included within the cabinet of dental control unit 52 in FIG. 1. Components below that line are outside the cabinet. A water supply 76 provides a source of water under pressure. An air supply 78 provides air under pressure to the dental control unit. It is to be appreciated that water and air supplies are used in connection with virtually all dental control units whether or not fiber optics are utilized inasmuch as a conventional dental drill requires both air and water to operate. Air supply 78 provides air under pressure to a foot switch 80 and a toggle switch 82. When the foot switch is depressed, the air under pressure is allowed to pass through shuttle valve 86 into another conduit 88 through T-connector 90 and into conduits 92, 94. Likewise, whenever the toggle switch is switched, air is allowed to travel into conduit 96 to conduit 88, etc.

A conventional water relay 97 is supplied via conductor 98 with water under pressure from supply 76. The relay has an input 100 responsive to air pressure, an input 102 for receipt of water under pressure, and an output 104. When air pressure is provided at input 100, relay 97 actuates and allows communication between input 102 and output 104 thus allowing a flow of water through the relay. When air pressure is removed, communication ceases and water flowing from output 104 stops.

An air electric switch 106 is provided with an air input 108 and switch terminals indicated generally at 110. When air under pressure is provided at input 108, contacts within 106 close, thus electrically connecting the wires appearing on terminals 110.

A heat sensor 112 has terminals 114, 116. Sensor 112, although shown separated from heat sink 12, is, when installed, bolted to the heat sink. When sensor 112 becomes heated beyond a certain temperature, in the instant embodiment 115° F., contacts within the sensor open thus electrically disconnecting the wires appearing on terminals 114, 116.

A needle valve 118 is provided to vary the flow of water which may be appearing in a conduit 120 to which it is connected. Valve 118 may be adjusted to either increase or decrease the flow permitted in conduit 120.

Finishing now the description of structure included within FIG. 5, a conventional transformer 122 receives 110-volts AC from a conventional outlet via plug 124 and transforms it to a 12 volt output on lines 126, such being ultimately provided to light 16.

Examining now the use and operation of the instant embodiment of the invention, in order to provide light within fiber-optic bundle 66, the end 68 of the fiber-optic bundle is inserted into one of ducts 18 until grip 72 is adjacent end face 30 of heat sink 12. It should be noted that the exposed fiber-optic bundle extending from grip 72 is of the same length as each of ducts 18. Thus, when so inserted, the tip of the fiber-optic bundle appears at bottom face 34 in cavity 14. It should be noted that the angle at which the ducts enter the cavity causes the bundle to point directly at filament 42.

When a dentist desires to utilize the fiber optics within cable 58 to view a patient's mouth, he may step on foot switch 80 thus supplying air to conduit 88 and via T-connector 90 to both relay 97 and switch 106. Electricity is provided via heat sensor 112 across wires 44, 46 thus lighting the light (assuming the sensor is not overheated, thus opening the circuit). Additionally, air flows to conduit 92 thus actuating relay 97 and permitting a flow of water from conduit 98 through the bore in the block to outlet 24 and through valve 118. The valve is adjusted to create a desired rate of flow for cooling the light. As the light is on, heat is transferred from the lamp into heat sink 12 and ultimately into the water which flows through the block, thus maintaining the light within the range of operating temperature.

Although not illustrated in FIG. 5, depression of foot switch 80 also activates the dentist's drill so that the light and the drill operate simultaneously. If the dentist should wish only the light, use may be made of light switch 82 which lights the light and begins the water flow, as did the foot switch, without operation of the drill. Thus, the dentist may use the light merely for examination without simultaneously running the drill. It is to be appreciated that four ducts 18 are provided in the event that the dentist has more than one handpiece, i.e., two separate drills each of which require lights and perhaps in addition, a separate handpiece used only for examination purposes and having only a fiber optic bundle for shining light into a patient's mouth.

It is noted that water flowing from the block and through valve 118 may either be drained away or may be supplied through syringe 56 for rinsing of the patient's mouth. Past syringes have utilized heating elements or have had separate water heaters for providing heated water thereto, necessitating continuous pumping of hot water through the syringe. When water from heat sink 12 is utilized, a conventional syringe may be used to supply warm water for use in spraying a patient's mouth.

It is to be appreciated that the instant embodiment of the invention is easily installed in existing control units inasmuch as air and water supplies are typically present.

While a preferred embodiment of the invention has been described, it is appreciated that variations and modifications may be made without departing from the spirit of the invention.

I claim:

1. Cooling apparatus for a light source which supplies light to an optical fiber, said apparatus comprising a heat-conductive heat sink body having means defining a cavity extending thereinto from a side of said body for receiving such a light source, means defining a duct extending into said body from another side of said body for permitting access of such a fiber to the source, and means defining a fluid coolant passage extending through said heat sink body; and a source of fluid coolant operatively connected to said passage for providing a flow of fluid coolant through said passage which operates to conduct heat away from the heat sink body.

2. The apparatus of claim 1, wherein said heat sink body is block-shaped, said cavity being at one end thereof and said passage-defining means is a bore which traverses the block about said cavity.

3. In dental apparatus, means for supplying light into a patient's mouth comprising:
- a heat-conductive heat sink body having a light source receiving cavity extending thereinto from a side of said body, a duct extending into said body from another side of said body joining with an inner portion of said cavity, and a coolant passage extending through said body out of communication with said cavity and duct,
- a high intensity light source mounted within said light source receiving cavity,
- an elongate optical fiber for transmitting light having one end mounted within said duct and exposed by said mounting to said light source, and
- a source of fluid coolant connected to said coolant passage for providing a flow of fluid coolant through said passage which operates to conduct heat away from said heat sink body.

4. The apparatus of claim 1 or 3 which further includes means for simultaneously activating said light source and said source of fluid coolant.

5. A method of cooling a high intensity light source which supplies light for transmission along an optical fiber comprising the steps of
- surrounding such a light source with a heat conductor having a duct for permitting access of such a fiber to the source and means defining a fluid transmission conduit through said conductor, and
- activating said light source, and
- transmitting fluid through said defining means to conduct heat away from said conductor.

* * * * *